US010239915B2

(12) United States Patent
Shinohara et al.

(10) Patent No.: US 10,239,915 B2
(45) Date of Patent: Mar. 26, 2019

(54) METHOD FOR CONTINUOUS PRODUCTION OF DEGRADATION PRODUCT OF WATER-INSOLUBLE POLYMERIC COMPOUND

(71) Applicants: JELLYFISH RESEARCH LABORATORIES, INC., Kawasaki-shi (JP); MARUWA OIL & FAT CO., LTD., Shinagawa-ku (JP)

(72) Inventors: Satoshi Shinohara, Kanagawa (JP); Takayuki Baba, Kanagawa (JP); Koji Kihira, Kanagawa (JP)

(73) Assignees: JELLYFISH RESEARCH LABORATORIES, INC., Kawasaki-shi (JP); MARUWA OIL & FAT CO., LTD., Shinagawa-ku (JP)

( * ) Notice: Subject to any disclaimer, the term of this patent is extended or adjusted under 35 U.S.C. 154(b) by 195 days.

(21) Appl. No.: 15/107,983

(22) PCT Filed: Dec. 17, 2014

(86) PCT No.: PCT/JP2014/083342
§ 371 (c)(1),
(2) Date: Jun. 24, 2016

(87) PCT Pub. No.: WO2015/098634
PCT Pub. Date: Jul. 2, 2015

(65) Prior Publication Data
US 2016/0326213 A1 Nov. 10, 2016

(30) Foreign Application Priority Data

Dec. 25, 2013 (JP) .................................. 2013-267662

(51) Int. Cl.
| C07K 1/12 | (2006.01) |
| C07K 14/47 | (2006.01) |
| C07K 14/78 | (2006.01) |
| C08B 37/00 | (2006.01) |
| C07K 2/00 | (2006.01) |
| C07K 14/435 | (2006.01) |

(52) U.S. Cl.
CPC ................ *C07K 1/122* (2013.01); *C07K 2/00* (2013.01); *C07K 14/435* (2013.01); *C07K 14/4741* (2013.01); *C07K 14/78* (2013.01); *C08B 37/0039* (2013.01)

(58) Field of Classification Search
CPC .... C07K 1/122; C07K 14/78; C07K 14/4741; C07K 2/00; C07K 14/435; C08B 37/0039
USPC ............... 536/124; 568/863; 127/37; 502/27
See application file for complete search history.

(56) References Cited

U.S. PATENT DOCUMENTS

| 4,534,906 A | 8/1985 | Johnston |
| 5,179,197 A | 1/1993 | Uchida et al. |
| 5,767,078 A | 6/1998 | Johnson et al. |
| 8,765,938 B2 | 7/2014 | Hara et al. |
| 8,945,309 B2 | 2/2015 | Fukuoka et al. |

FOREIGN PATENT DOCUMENTS

| CN | 101691617 A | 4/2010 |
| CN | 101692617 A | 4/2010 |
| JP | 59-98096 A | 6/1984 |
| JP | 4-211100 A | 8/1992 |
| JP | 2000-212108 A | 8/2000 |
| JP | 2007-51191 A | 3/2007 |
| JP | 2008-31106 A | 2/2008 |
| JP | 2009-120511 A | 6/2009 |
| JP | 2011-46686 A | 3/2011 |
| JP | 2011-213634 A | 10/2011 |
| JP | 2012-31107 A | 2/2012 |
| JP | 2012-41395 A | 3/2012 |
| JP | 2012-97118 A | 5/2012 |
| JP | 2013-6142 A | 1/2013 |

(Continued)

OTHER PUBLICATIONS

Masuda et al. Automated Protein Hydrolysis Delivering Sample to a Solid Acid Catalyst for Amino Acid Analysis. Anal. Chem. 82, 8939-8945, 2010. (Year: 2010).*
Extended European Search Report dated Oct. 9, 2017 in Patent Application No. 14873187.0.
Satoshi Suganuma, et al., "Cellulose saccharification using solid acid," Abstracts of Meeting A, 100$^{th}$ Meeting of Catalysis Society of Japan (CATSJ), Sep. 17, 2007, p. 85 (with partial translation) (4 pages).
International Search Report dated Mar. 10, 2015 in PCT/JP2014/083342 filed Dec. 17, 2014.

*Primary Examiner* — Yih-Horng Shiao
(74) *Attorney, Agent, or Firm* — Oblon, McClelland, Maier & Neustadt, L.L.P.

(57) ABSTRACT

This invention is intended to produce a novel functional material through solubilization and molecular weight reduction of a water-insoluble polymeric compound, such as a water-insoluble protein or water-insoluble polysaccharide, in a simple and efficient manner. This invention provides a method for producing a degradation product of a water-insoluble polymeric compound comprising the steps of: bringing a water-insoluble polymeric compound into contact with a solid acid catalyst, heating the resulting mixture, and recovering a supernatant; adding an aqueous medium to the solid acid catalyst after the supernatant is recovered, agitating and heating the resulting mixture, and recovering a supernatant; washing the solid acid catalyst with an aqueous medium and recovering a wash solution; mixing the recovered supernatant with the wash solution, so as to obtain a fraction that has not adsorbed to the solid acid catalyst; and eluting an adsorbed fraction from the solid acid catalyst and recovering an eluate, so as to obtain a fraction that has adsorbed to the solid acid catalyst.

13 Claims, 12 Drawing Sheets

(56) References Cited

FOREIGN PATENT DOCUMENTS

| | | |
|---|---|---|
| JP | 2013-95708 A | 5/2013 |
| WO | 2007/100052 A1 | 9/2007 |
| WO | 2008/001698 A1 | 1/2008 |

* cited by examiner

Fig. 3
a
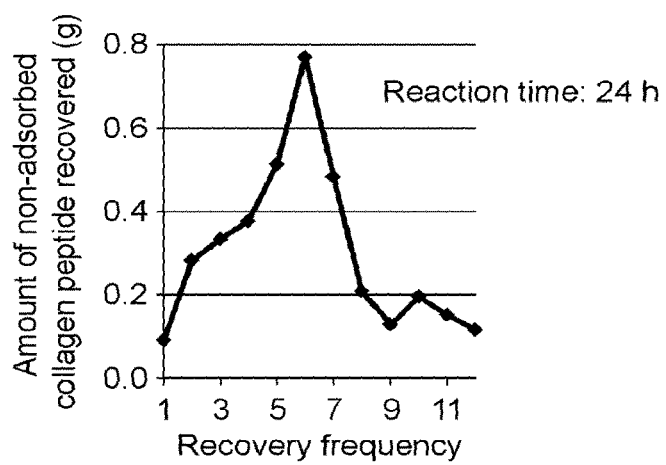
b
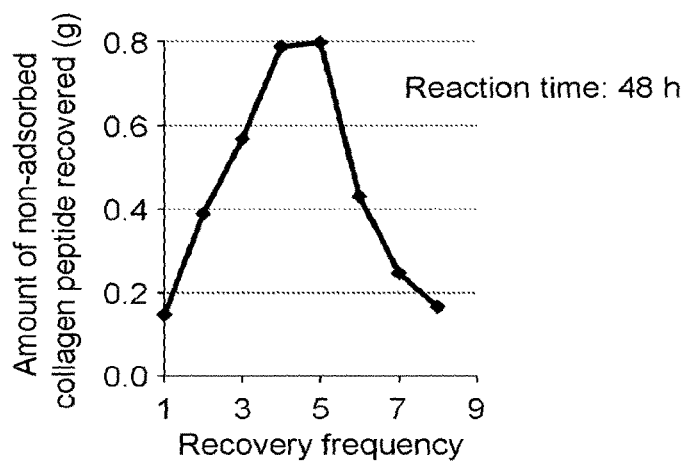
c
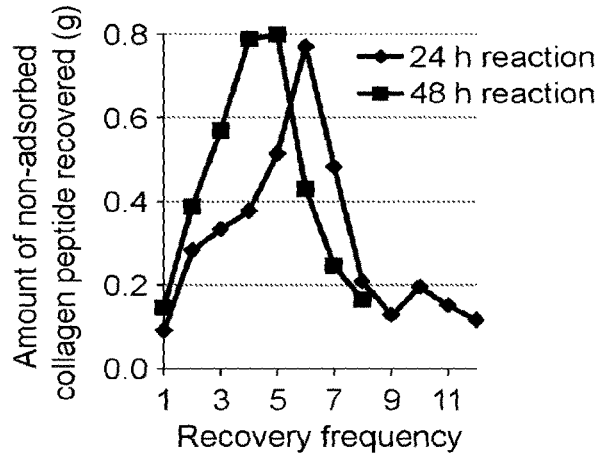

Fig. 5
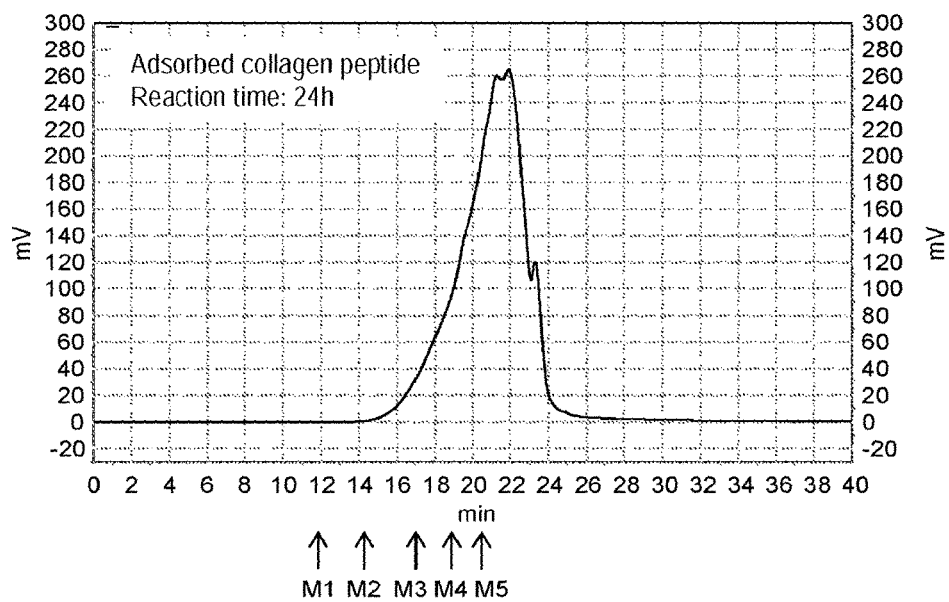
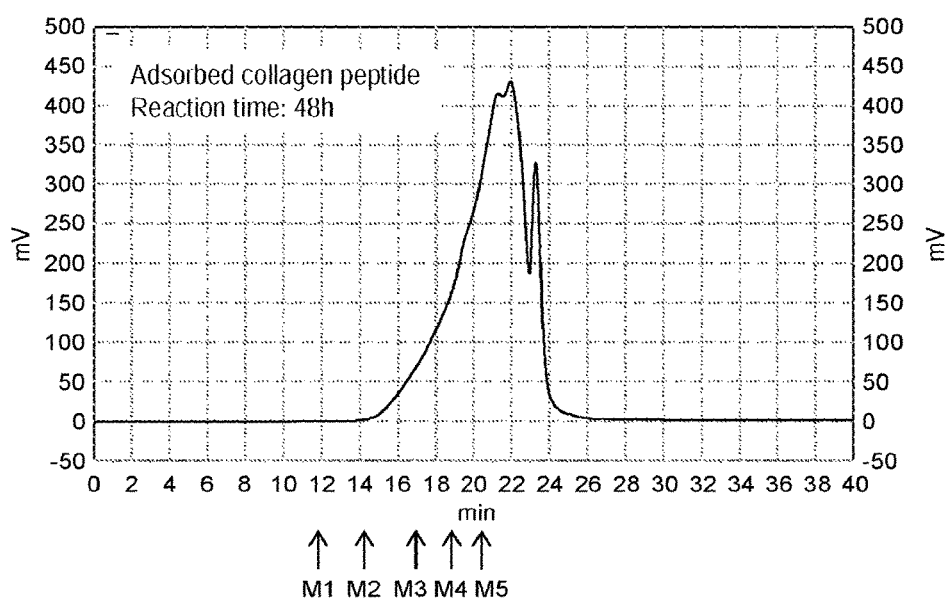

Fig. 7
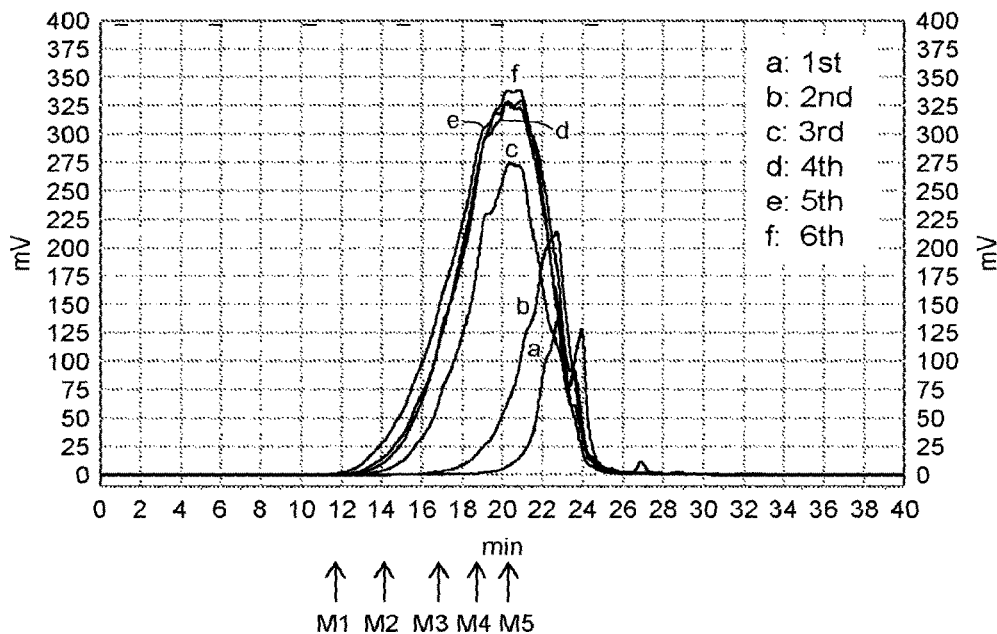
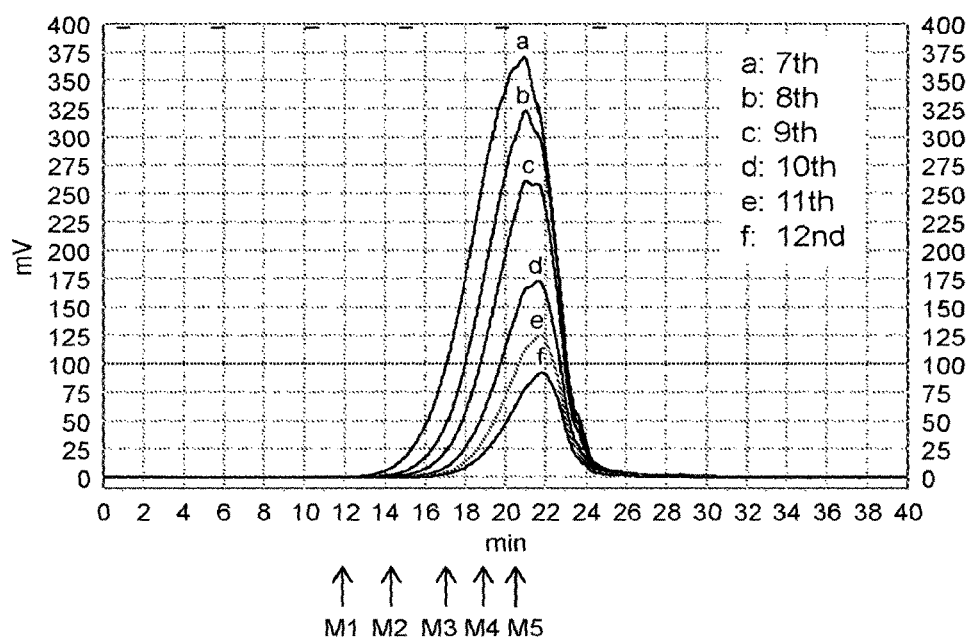

Fig. 9
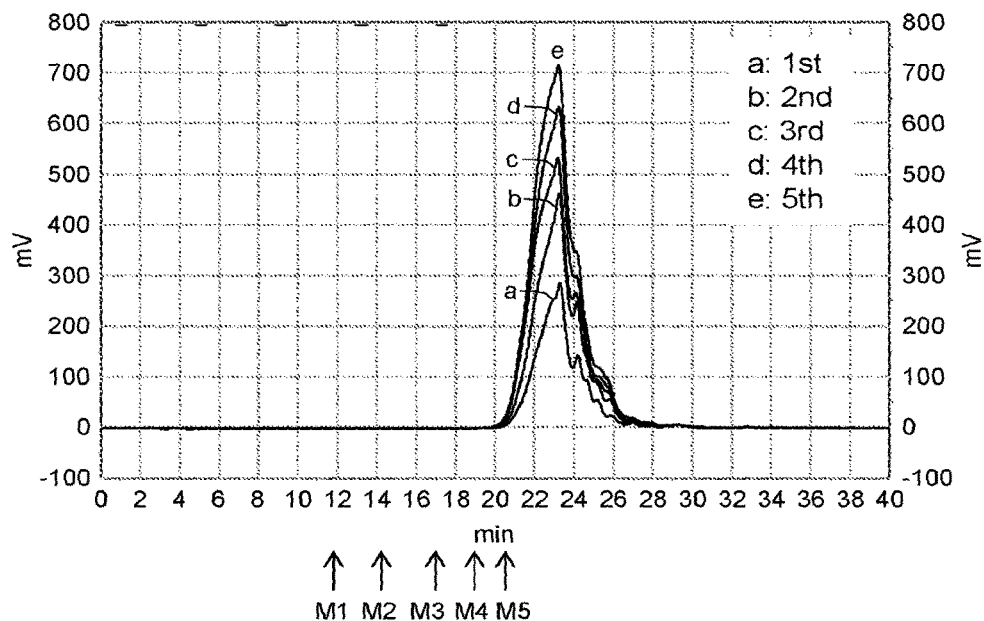
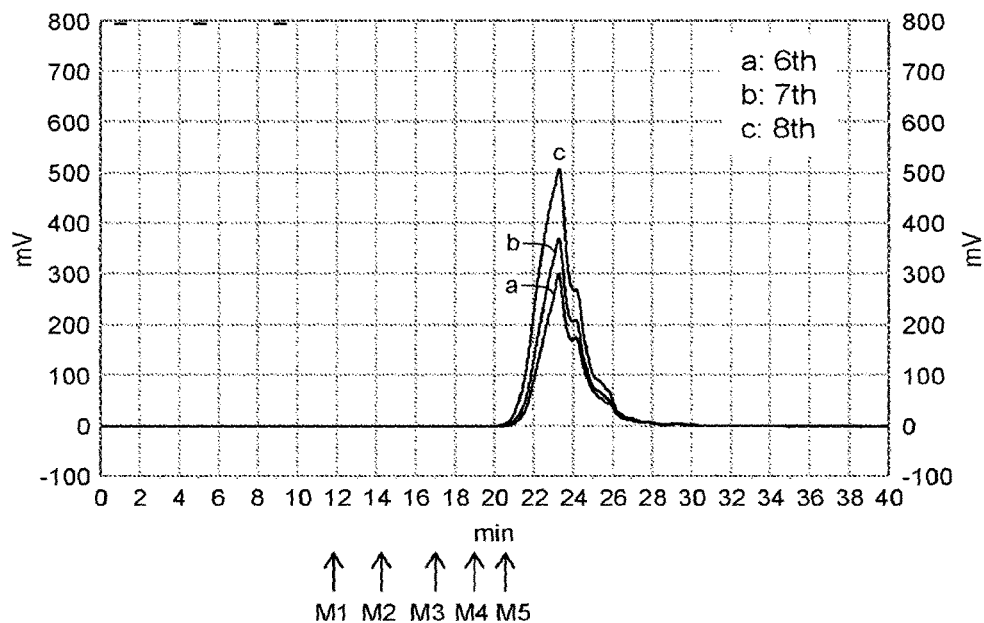

METHOD FOR CONTINUOUS PRODUCTION OF DEGRADATION PRODUCT OF WATER-INSOLUBLE POLYMERIC COMPOUND

TECHNICAL FIELD

The present invention relates to a method of solubilizing and reducing the molecular weight of a water-insoluble polymeric compound (a protein or polysaccharide), so as to continuously produce a degradation product of a water-insoluble polymeric compound (a protein or polysaccharide).

BACKGROUND ART

In recent years, functional proteins and functional peptides have gained attention as materials for pharmaceutical products, food and beverage products, and cosmetic products. In particular, collagen, which has effects of alleviating symptoms associated with bone and joint disorders, effects of making the skin beautiful, effects of osteogenesis, and other effects, as well as collagen peptide, which is a degradation product thereof, have been noted as representative examples of such functional proteins or functional peptides. Major raw materials for collagen or collagen peptide are, for example, the skin, the bones, and the tendons of fish, cows, pigs, and chicken, and jellyfish is one such raw materials. A method comprising subjecting a jellyfish to a treatment process, such as freezing, thawing, low temperature storage, and agitation so as to efficiently recover undenatured collagen from such jellyfish has been proposed (e.g., Patent Document 1 and Patent Document 2).

The recent jellyfish outbreaks in coastal areas of Japan are serious social problems and have caused tremendous damage to the fishery industry. In addition, the removal and disposal of jellyfish gathered around the water intakes of factories and power generation plants are cost-consuming. Accordingly, it is desirable that jellyfish be effectively used as a collagen raw material as described above. To date, a major type of jellyfish used as a collagen raw material has been *Aurelia aurita* because of its small size and liquescent properties, but a jellyfish that is large and has large water-insoluble protein content, such as *Rhopilema esculenta*, has not yet been effectively used.

In general, water-insoluble proteins are solubilized and the molecular weight thereof is reduced via heating treatment, acid or alkali treatment, treatment with a protease, or other means. However, some proteins that have been subjected to heating treatment may become thermally denatured, disadvantageously. When acid or alkali treatment is employed, amino acid may become destroyed, and disposal after the treatment is also cost-consuming and laborious. In addition, protease treatment requires adequate determination and regulation of temperature and pH level, so as to provide optimal conditions for an enzyme to be used. When an enzyme remains in the treated product, inactivation and removal of such enzyme become necessary.

A method of protein hydrolysis involving the use of a solid acid catalyst is known (Patent Document 3), and such method has been employed for the production of jellyfish collagen peptide (Patent Document 4). In these examples, however, soluble proteins are targeted, and water-insoluble proteins are not subjected to solubilization or molecular weight reduction.

Meanwhile, a technique for degrading a lignocellulose constituted by cellulose, hemicellulose, and lignin has been studied as a means for effective use of ligneous biomass resources, although such technique suffers from similar problems as those occurring in the case of the water-insoluble proteins described above. For example, acid saccharification and enzymatic saccharification are techniques available for lignocellulose degradation. Acid saccharification, which involves the use of sulfuric acid, is advantageous in terms of high reaction speed; however, this technique is problematic in terms of hyperdegradation of a certain product (a monosaccharide), and waste acid solution disposal is problematic in terms of environmental burdens. While enzymatic saccharification involving the use of a cellulase enzyme is advantageous in that it imposes lighter environmental burdens, cellulose has a water-insoluble, strong crystalline structure in which β-glucose molecules are polymerized via a 1,4-glucoside bond and the resulting polymers are bound to each other via a hydrogen bond. Thus, the contact area between such cellulose and cellulase enzyme is small, and the reaction speed is low, disadvantageously.

PRIOR ART DOCUMENTS

Patent Documents

Patent Document 1: JP 2007-051191 A
Patent Document 2: JP 2008-031106 A
Patent Document 3: JP 2009-120511 A
Patent Document 4: JP 2013-95708 A

SUMMARY OF THE INVENTION

Problem to be Solved by the Invention

It is an object of the present invention to produce a new functional material through solubilization and molecular weight reduction of a water-insoluble polymeric compound, such as a water-insoluble protein or a water-insoluble polysaccharide, in a simple manner with high efficiency.

Means for Solving the Problem

The present inventors have conducted concentrated studies in order to attain the above object. As a result, surprisingly, they discovered that a degradation product of a water-insoluble protein could be primarily obtained in a fraction that has not adsorbed to a solid acid catalyst (hereafter referred to as a "non-adsorbed fraction") as a result of treatment of the water-insoluble protein with a solid acid catalyst. After a procedure of recovering the non-adsorbed fraction has been repeated, an adsorbed fraction eluted from the solid acid catalyst may also be combined therewith. Thus, the present inventors succeeded in continuously producing a water-insoluble protein degradation product at high yield, thereby completing the present invention.

Specifically, the present invention includes the following.
(1) A method for producing a degradation product of a water-insoluble polymeric compound comprising the following steps:
(A) bringing a water-insoluble polymeric compound into contact with a solid acid catalyst, heating the resulting mixture, and recovering a supernatant;
(B) following Step (A), adding an aqueous medium to the solid acid catalyst, agitating and heating the resulting mixture, and recovering a supernatant;
(C) following Step (B), washing the solid acid catalyst with an aqueous medium and recovering a wash solution;

(D) mixing the supernatant recovered in Step (A), the supernatant recovered in Step (B), and the wash solution recovered in Step (C) and obtaining a fraction that has not adsorbed to the solid acid catalyst; and (E) following Step (D), eluting the adsorbed fraction from the solid acid catalyst and recovering an eluate, so as to obtain a fraction that has adsorbed to the solid acid catalyst.

(2) The method according to (1), wherein the water-insoluble polymeric compound is a water-insoluble protein or a water-insoluble polysaccharide.

(3) The method according to (1) or (2), which further comprises a step of soaking the water-insoluble polymeric compound in an aqueous medium before the step of bringing the water-insoluble polymeric compound into contact with the solid acid catalyst.

(4) The method according to any of (1) to (3), wherein the amount of the water-insoluble polymeric compound is 0.01- to 0.5-fold relative to the amount of the solid acid catalyst by mass.

(5) The method according to any of (1) to (4), wherein, in Step (A), the amount of an aqueous medium used when bringing the water-insoluble polymeric compound into contact with the solid acid catalyst is adjusted to 1- to 50-fold relative to the amount of the solid acid catalyst by mass.

(6) The method according to any of (1) to (5), wherein the heating treatment in Step (A) and Step (B) is carried out at 40° C. to 160° C. for 0.1 to 168 hours.

(7) The method according to any of (1) to (6), wherein Step (A) and Step (B) are each repeated a plurality of times until the yield of the degradation product of the water-insoluble polymeric compound in the non-adsorbed fraction reaches 50% or higher.

(8) The method according to any of (1) to (7), wherein the solid acid catalyst is at least one member selected from the group consisting of a cation exchanger, zeolite, and diatomaceous earth.

Effects of the Invention

The present invention provides a method for producing a degradation product of a water-insoluble polymeric compound. According to the method of the present invention, a degradation product of a water-insoluble polymeric compound can be continuously produced with high efficiency in a cost-effective manner from a material that was impossible to effectively use in the past. Unlike conventional techniques using heating treatment, acid or alkali treatment, protein degradation, or glycolytic enzyme treatment, the method of the present invention does not cause unnecessary denaturation of a polymeric compound, hydrolysis of such compound can be performed with certainty, and the production step does not require complicated operations or special regulations.

This patent application claims priority from Japanese Patent Application No. 2013-267662 filed on Dec. 25, 2013, and it includes part or all of the contents as disclosed in the description thereof.

BRIEF DESCRIPTION OF THE DRAWINGS

FIG. 3 shows a transition in the amount of a degradation product of a water-insoluble polymeric compound recovered from a fraction that has not adsorbed to a solid acid catalyst (i.e., a collagen peptide obtained from the *Rhopilema esculenta* umbrella) (FIG. 3*a*: reaction time: 24 hours; FIG. 3*b*: reaction time: 48 hours) and a comparison of the absorbed amount depending on reaction time (FIG. 3*c*).

FIG. 5 shows molecular weight distribution of a degradation product of a water-insoluble polymeric compound in a fraction that has adsorbed to a solid acid catalyst (i.e., a collagen peptide obtained from the *Rhopilema esculenta* umbrella) (upper diagram: reaction time: 24 hours; lower diagram: reaction time: 48 hours; the molecular weights of pullulan standards: M1: 112 kDa; M2: 47.3 kDa; M3: 22.8 kDa; M4: 11.8 kDa; M5: 5.9 kDa).

FIG. 7 shows molecular weight distribution of a degradation product of a water-insoluble polymeric compound (a sericin peptide) in a fraction that has not adsorbed to a solid acid catalyst (upper diagram: the first to the sixth recovered liquids; lower diagram: the seventh to the twelfth recovered liquids; the molecular weights of pullulan standards: M1: 112 kDa; M2: 47.3 kDa; M3: 22.8 kDa; M4: 11.8 kDa; M5: 5.9 kDa).

FIG. 9 shows molecular weight distribution of a degradation product of a water-insoluble polymeric compound (a keratin peptide) in a fraction that has not adsorbed to a solid acid catalyst (upper diagram: the first to the fifth recovered liquids; lower diagram: the sixth to the eighth recovered liquids, the molecular weights of pullulan standards: M1: 112 kDa; M2: 47.3 kDa; M3: 22.8 kDa; M4: 11.8 kDa; M5: 5.9 kDa).

EMBODIMENTS FOR CARRYING OUT THE INVENTION

Hereafter, the present invention is described in detail.

Figure 1:
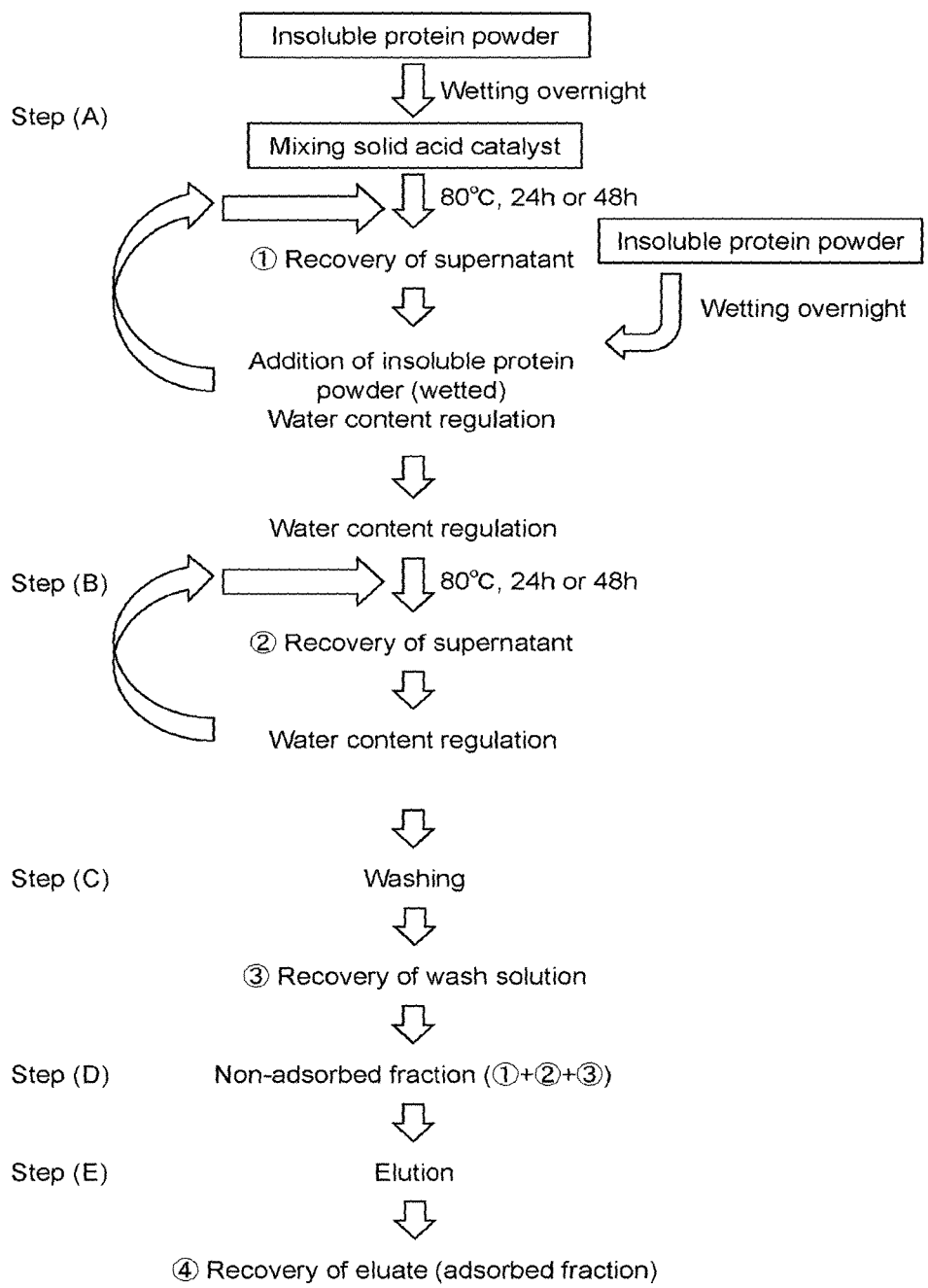
FIG. 1 shows the process chart of the method for continuously producing a degradation product of a water-insoluble polymeric compound according to an embodiment of the present invention.

The present invention provides a method for producing a degradation product of a water-insoluble polymeric compound, which comprises the steps described below. FIG. 1 schematically shows the process of production.

(A) A step of bringing a water-insoluble polymeric compound into contact with a solid acid catalyst, heating the resulting mixture, and recovering a supernatant;

(B) following Step (A), a step of adding an aqueous medium to the solid acid catalyst, agitating and heating the resulting mixture, and recovering a supernatant;

(C) following Step (B), a step of washing the solid acid catalyst with an aqueous medium and recovering a wash solution;

(D) a step of mixing the supernatant recovered in Step (A), the supernatant recovered in Step (B), and the wash solution recovered in Step (C) and obtaining a fraction that has not adsorbed to the solid acid catalyst; and (E) following Step (D), a step of eluting the adsorbed fraction from the solid acid catalyst and recovering an eluate, so as to obtain a fraction that has adsorbed to the solid acid catalyst.

A "water-insoluble polymeric compound" used in the method of the present invention is preferably a water-insoluble protein or a water-insoluble polysaccharide. In the present invention, "a degradation product of a water-insoluble polymeric compound" may be a product resulting from solubilization and degradation of a water-insoluble polymeric compound, and the average molecular weight and the molecular weight distribution thereof are not limited.

Step (A):

Step (A) comprises bringing a water-insoluble polymeric compound into contact with a solid acid catalyst, heating the resulting mixture, and recovering a supernatant. The term "water-insoluble" used in the present invention refers to a condition under which a substance of interest does not dissolve in water.

"Water-insoluble polymeric compounds" encompass water-insoluble proteins and water-insoluble polysaccharides, such substances may be derived from animals or plants, and types thereof are not particularly limited. Examples of water-insoluble proteins include collagen, sericin, fibroin, keratin, casein, albumin, globulin, elastin, myosin, actin, whey protein, soybean protein, wheat protein, sesame protein, and egg protein. Jellyfish collagen is particularly preferable. While jellyfish species is not limited, examples of jellyfish include *Rhopilema esculenta, Stomolophus, Mastigias papua, Thysanostoma thysanura, Netrostoma setouchianum, Cephea cephea, Rhopilema asamushi,* and *Cassiopea ornate* belonging to Rhizostomeae, Scyphozoa. Examples of water-insoluble polysaccharides include cellulose, hemicellulose, lignocellulose, inulin, pectin, glucan, carragheenan, agarose, chitin, and chitosan. Raw materials of water-insoluble polymeric compounds are preferably roughly ground, and more preferably powdered, with the use of a shearing machine, a mincing machine, a cutter, or the like as a pre-treatment, so as to promote solubilization and molecular weight reduction caused upon contact with a solid acid catalyst. Powderization can be carried out with the use of an apparatus that is generally used by a person skilled in the art, such as a hammer mill, bead mill, roller mill, pin mill, or blender.

A water-insoluble polymeric compound that has been subjected to a pre-treatment as described above may be wetted with an aqueous medium before it is brought into contact with a solid acid catalyst. A water-insoluble polymeric compound is preferably subjected to wetting for approximately 1 to 36 hours, although such period varies depending on water-insoluble polymeric compound type.

A solid acid catalyst used in the present invention is preferably at least one member selected from the group consisting of a cation exchanger, zeolite, and diatomaceous earth, with a cation exchanger being more preferable. Such solid acid catalyst can be used alone or in combinations of two or more.

A cation exchanger is preferably a resin comprising at least either a sulfone group or a carboxyl group, and a sulfone group and a carboxyl group may be a sulfopropyl group and a carboxymethyl group, respectively. When a counter ion of a cation exchanger is not a proton, it is preferable that the cation exchanger be used after its counter ion has been substituted with a proton. A sulfonic acid cation exchanger is an ion exchanger capable of exchanging cations including a sulfonic acid group ($-SO_3H$). Examples of preferable forms include a cation exchange resin comprising a sulfonic acid group and a cation exchange membrane comprising a sulfonic acid group. Examples of preferable cation exchange resins include a resin comprising a hydrophilic vinyl polymer as a substrate, such as TOYOPEARL SP-650C and TOYOPEARL SP-550C (manufactured by Tosoh Corporation), and a polytetrafluoroethylene copolymer comprising perfluorosulfonic acid, such as Nafion®.

Any zeolite that is generally used as a zeolite catalyst can be used without particular limitation. An example thereof is Zeolum® (manufactured by Tosoh Corporation).

Any type of diatomaceous earth that can function as an acid catalyst can be used without particular limitation. An example thereof is diatomaceous earth (granular) manufactured by Wako Pure Chemical Industries, Ltd.

A solid acid catalyst used in the present invention may be in either a particulate or powdered form. It is preferable that the average particle diameter be approximately 2 μm to 2 mm and the ion exchange capacity be approximately 0.01 to 1 eq/l.

The solid acid catalyst is preferably a porous material. For example, TOYOPEARL SP-650C and TOYOPEARL SP-550C (manufactured by Tosoh Corporation) are made of a porous material comprising a gel filtration chromatography filler into which a sulfonic acid group as an ion exchange group. The adequate pore size of a porous material varies depending on the molecular weight of the target water-insoluble polymeric compound. For example, it is 0.01 to 0.75 μm, and preferably 0.05 to 0.6 μm.

When the water-insoluble polymeric compound is brought into contact with the solid acid catalyst, the amount of the aqueous medium is, in combination with the aqueous medium used for wetting the water-insoluble polymeric compound, 1 to 50 times and preferably 5 to 15 times greater than the amount of the solid acid catalyst by mass. According to the method of the present invention, a degradation product of a water-insoluble polymeric compound is mainly recovered from a fraction that has not adsorbed to the solid acid catalyst (i.e., a supernatant). When the amount of the aqueous medium is below the lower limit of the aforementioned range, centrifugation is required, and, accordingly, such an amount is not preferable. Also, an amount of the aqueous medium exceeding the upper limit of the aforementioned range is not preferable because of lowered working efficiency. In the present invention, the aqueous medium used for wetting the water-insoluble polymeric compound and for bringing the water-insoluble polymeric compound into contact with the solid acid catalyst is not particularly limited, provided that such aqueous medium does not inhibit the reaction between the water-insoluble polymeric compound and the solid acid catalyst. Examples thereof include water, such as ion exchange water, purified water, RO water, tap water, and well water; buffers, such as phosphate, carbonate, acetate, borate, citrate, and Tris buffers; and aqueous solutions of inorganic salts, such as sodium chloride, potassium chloride, and calcium chloride. The salt concentration is preferably as low as approximately 1 mM to 0.1 M.

The amount of the water-insoluble polymeric compound can be adequately determined in accordance with the catalytic ability of the solid acid catalyst. For example, such amount is 0.01 to 0.5 times and preferably 0.05 to 0.2 times greater than the amount of the solid acid catalyst by mass.

After the solid acid catalyst has been brought into contact with the water-insoluble polymeric compound, heating treatment is necessary, so as to satisfactorily perform solubilization and molecular weight reduction of the water-insoluble polymeric compound. The heating temperature is 40° C. to 160° C., preferably 60° C. to 120° C., and more preferably 80° C. to 100° C. The heating time is 0.1 to 168 hours, preferably 10 to 72 hours, and more preferably 24 to 48 hours, although it varies depending on the heating temperature. When a water-insoluble polymeric compound is a water-insoluble protein, for example, it is important to stop the molecular weight reduction until degradation of the protein to a peptide. When heating treatment is performed at high temperature over a long period of time, disadvantageously, a water-insoluble protein may be hydrolyzed to an amino acid. Accordingly, the treatment period is preferably shortened as the treatment temperature is increased.

In the present invention, the water-insoluble polymeric compound is preferably brought into contact with the solid acid catalyst by the batch method. In such a case, the solid acid catalyst is thoroughly mixed with the water-insoluble polymeric compound in the container, and the mixture is then heated. Heating is preferably carried out after the container has been hermetically sealed. Heating conditions are as described above. The batch method may involve the use of one or more containers.

Figure 2:
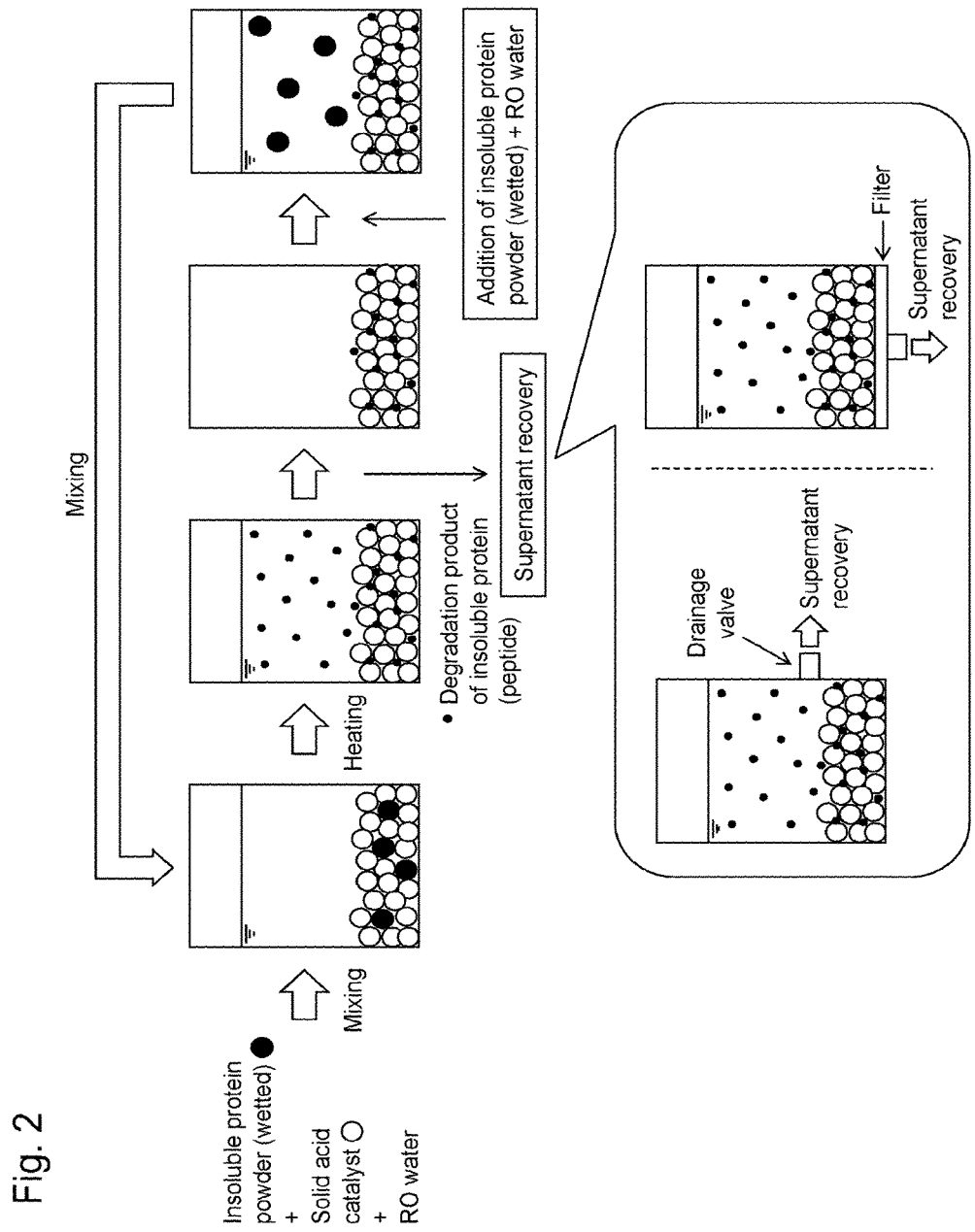
FIG. 2 shows an embodiment of a method for recovering a fraction that has not adsorbed to a solid acid catalyst (a supernatant) in the method for continuously producing a degradation product of a water-insoluble polymeric compound according to an embodiment of the present invention.

A supernatant is recovered after the heating treatment. A supernatant can be recovered via sedimentation, floatation, filtration, membrane separation, centrifugation, or another technique, and sedimentation is preferable because of the simplicity of the process. FIG. 2 shows an embodiment of the method for supernatant recovery. A solid acid catalyst is heavier than an aqueous medium. If it is allowed to stand, accordingly, sedimentation generally takes place within approximately 15 minutes. During actual implementation, a drainage valve may be provided in a position slightly little above the tank bottom (slightly above the position of the sedimented solid acid catalyst), and the liquid may be discharged therefrom, so as to recover a supernatant. Alternatively, a filter having a pore diameter that allows a supernatant comprising a degradation product of a water-insoluble polymeric compound to pass therethrough but does not allow a solid acid catalyst to pass therethrough may be provided at the bottom of the tank, and the liquid may be discharged therefrom. Thus, a supernatant can be recovered.

A series of procedure in this step (i.e., contact of a water-insoluble polymeric compound with a solid acid catalyst, heating treatment, and recovery of a supernatant) is repeated a plurality of times. The number of repetitions can be adequately changed in accordance with the water-insoluble polymeric compound type and the target yield of this step. For example, such procedure may be repeated 4 or 5 times. The number of repetitions may be determined so as to adjust the yield of the degradation product of the water-insoluble polymeric compound to 50% or higher, preferably 65% or higher, more preferably 70% or higher, and most preferably 80% or higher in the non-adsorbed fraction obtained by mixing the supernatant recovered in this step, the supernatant recovered in the next Step (B), and the wash solution recovered in the next Step (C) together. Every time the water-insoluble polymeric compound is brought into contact with the solid acid catalyst, the entire amount of the water-insoluble polymeric compound to be treated is preferably divided into fractions of equal amounts from the viewpoint of the efficiency of solubilization and molecular weight reduction of the water-insoluble polymeric compound with the aid of the solid acid catalyst.

Step (B):

Following Step (A), Step (B) comprises adding an aqueous medium to the solid acid catalyst, agitating and heating the resulting mixture, and recovering a supernatant. Through this step, a water-insoluble polymeric compound remaining unsolubilized in Step (A) and adhering to the solid acid catalyst surface can be solubilized, the molecular weight thereof can be reduced, and the resulting water-insoluble polymeric compound can be recovered. In this step, heating treatment may be carried out in accordance with the heating conditions (temperature and duration) that are employed when the solid acid catalyst is brought into contact with the water-insoluble polymeric compound. In this step, the recovery procedure is preferably repeated a plurality of times. The number of repetitions can be adequately changed in accordance with the water-insoluble polymeric compound type, the yield of the degradation product of the water-insoluble polymeric compound in Step (A), and the final target yield. For example, such procedure can be repeated 3 to 6 times. The number of repetitions may be determined so as to adjust the yield of the degradation product of the water-insoluble polymeric compound to 50% or higher, preferably 65% or higher, more preferably 70% or higher, and most preferably 80% or higher of the total amount of the non-adsorbed fraction obtained by mixing the supernatant recovered in Step (A), the supernatant recovered in Step (B), and the wash solution recovered in the next Step (C) together. A supernatant may be recovered in the same manner as in Step (A).

Step (C):

Following Step (B), Step (C) comprises washing a solid acid catalyst with an aqueous medium and recovering a wash solution. In this step, heating treatment is not carried out, and a solid acid catalyst may be washed once with an aqueous medium.

Step (D):

Step (D) comprises mixing the supernatant recovered in Step (A), the supernatant recovered in Step (B), and the wash solution recovered in Step (C) and obtaining a fraction that has not adsorbed to the solid acid catalyst. Through this step, a water-insoluble polymeric compound that has achieved solubilization and molecular weight reduction as a result of the reaction with the solid acid catalyst and has not adsorbed to the solid acid catalyst can be obtained with high yield.

Step (E):

Following Step (D), Step (E) comprises eluting the adsorbed fraction from the solid acid catalyst and recovering an eluate, so as to obtain a fraction that has adsorbed to the solid acid catalyst. Elution can be carried out with the use of, for example, an aqueous solution containing a salt such as sodium chloride at high concentration (0.1 M or more), an acid such as hydrochloric acid or trifluoroacetic acid, and a base such as triethylamine. According to the method of the present invention, the degradation product of a water-insoluble polymeric compound can be obtained with high yield by implementing the process from Step (A) to Step (D). Through Step (E), in addition, the degradation product of a water-insoluble polymeric compound adsorbed to the solid acid catalyst can be obtained from among the degradation product of a water-insoluble polymeric compound that has achieved solubilization and molecular weight reduction as a result of the reaction with the solid acid catalyst, and the yield can be further increased.

The non-adsorbed fraction obtained in Step (D) and the adsorbed fraction obtained in Step (E) may be independently dried and prepared into the form of the final product. Alternatively, these fractions may be mixed, dried, and then prepared in the form of the final product. Drying techniques are not particularly limited, and examples of such techniques include air drying, lyophilization, blow drying, hot-air drying, vacuum dehydration, and drying via microwave application.

EXAMPLES

Hereafter, the present invention is described in greater detail with reference to the examples, although the present invention is not limited to these examples.

Example 1

Solubilization and Molecular Weight Reduction of Insoluble Collagen from the *Rhopilema esculenta* Umbrella (1) Preparation of Insoluble Collagen from the *Rhopilema esculenta* Umbrella The body of *Rhopilema esculenta* sampled from the Ariake sea, Yanagawa, Fukuoka, Japan, was divided into the umbrella and the oral arm. After the brown skin inside the umbrella had been peeled, the umbrella was washed with tap water, and it was disinfected via washing with slightly acidic electrolyzed water and ozone water. A 1-kg of umbrella was cut from *Rhopilema esculenta* individuals and broken into 1-mm to 1-cm horn-shaped fractions. The resultant was filtered through gauze and a solid containing insoluble collagen was obtained. The solid was suspended in 9 times its volume of RO water and then the solid was recovered via filtration. This procedure was repeated 2 more times for the purpose of washing and desalting. The recovered solid was lyophilized and then powdered using a blender. Thus, insoluble collagen powder was obtained.

(2) Solubilization and Molecular Weight Reduction of Insoluble Collagen from the *Rhopilema esculenta* Umbrella Using Solid Acid Catalyst (2-1) Reaction Time: 24 Hours The insoluble collagen powder prepared in (1) (1 g) was wetted with 90 ml of RO water overnight, it was then mixed with 10 ml of cation exchange resin (TOYOPEARL SP-550C), and the mixture was thoroughly agitated. The resultant was subjected to reaction at 80° C. for 24 hours for solubilization, the resultant was cooled, and the supernatant containing the collagen peptide was then recovered. Subsequently, insoluble collagen powder obtained from the *Rhopilema esculenta* umbrella prepared in (1) was wetted overnight in the same manner as described above, the wet powder was added to the above cation exchange resin after the supernatant was recovered, the amount of the solution was adjusted to 100 ml with the addition of RO water, and the solution was thoroughly agitated. The resultant was subjected to reaction at 80° C. for 24 hours, and the supernatant was recovered again. This procedure was repeated 3 more times (and the first to the fifth recovery procedures were completed). The insoluble collagen powder obtained from the *Rhopilema esculenta* umbrella was subjected to each procedure in an equivalent amount (5 g in total).

RO water was added to the remaining cation exchange resin, so as to adjust the amount of the solution to 100 ml, and the resultant was thoroughly agitated. After the reaction had been conducted at 80° C. for 24 hours, the supernatant was recovered. This procedure was repeated 6 more times (and the sixth to the eleventh recovery procedures were completed). The remaining cation exchange resin was washed with 30 ml of RO water. The recovered supernatant was mixed with the wash solution, and a solution of the collagen peptide with a molecular weight (Mp) of 12 kDa or less, which had not adsorbed to the cation exchange resin, was obtained.

FIG. 3a shows the transition of the amount of the collagen peptide (i.e., the non-adsorbed peptide) in the recovered supernatant (reaction time: 24 hours).

Subsequently, 30 ml of 0.5 M NaCl was added to the washed cation exchange resin, and a degradation product containing the collagen peptide was eluted from the resin. This procedure was repeated 3 more times, and all the eluates were mixed with each other. Thus, a solution of the collagen peptide with a molecular weight (Mp) of 12 kDa or less, which had adsorbed to the cation exchange resin, was obtained.

(2-2) Reaction Time: 48 Hours

The insoluble collagen powder prepared in (1) (1 g) was wetted with 90 ml of RO water overnight, it was then mixed with 10 ml of cation exchange resin (TOYOPEARL SP-550C), and the mixture was thoroughly agitated. The resultant was subjected to reaction at 80° C. for 48 hours for solubilization, the reaction product was cooled, and the supernatant containing the collagen peptide was then recovered. Subsequently, the insoluble collagen powder obtained from the *Rhopilema esculenta* umbrella prepared in (1) was wetted overnight in the same manner as described above, the wet powder was added to the above cation exchange resin after the supernatant was recovered, and the amount of the solution was adjusted to 100 ml with the addition of RO water, followed by thorough agitation. The resultant was subjected to reaction at 80° C. for 48 hours, and a supernatant was recovered again. This procedure was repeated 3 more times (and the first to the fifth recovery procedures were completed). The insoluble collagen powder obtained from the *Rhopilema esculenta* umbrella was subjected to each procedure in an equivalent amount (5 g in total).

RO water was added to the remaining cation exchange resin, so as to adjust the amount of the solution to 100 ml, and the resultant was thoroughly agitated. After the reaction had been conducted at 80° C. for 48 hours, the supernatant was recovered. This procedure was repeated 2 more times (and the sixth to the eighth recovery procedures were completed). The remaining cation exchange resin was washed with 80 ml of RO water. The recovered supernatant was mixed with the wash solution, and a solution of the collagen peptide with a molecular weight (Mp) of 12 kDa or less, which had not adsorbed to the cation exchange resin, was obtained.

FIG. 3b shows the transition of the amount of the collagen peptide (i.e., the non-adsorbed peptide) in the recovered supernatant (reaction time: 48 hours).

Subsequently, 50 ml of 0.5 M NaCl was added to the washed cation exchange resin, and a degradation product containing the collagen peptide was eluted from the resin. This procedure was repeated 2 more times, and all the eluates were mixed with each other. Thus, a solution of the collagen peptide with a molecular weight (Mp) of 12 kDa or less, which had adsorbed to the cation exchange resin, was obtained.

(3) Quantification of Peptide Mixture (3-1) Preparation of Standard Collagen Peptide Sample The insoluble collagen powder obtained from the *Rhopilema esculenta* umbrella (1 g) was wetted with 100 ml of RO water overnight, it was then mixed with 100 g of cation exchange resin (TOYOPEARL SP-550C), and the mixture was thoroughly agitated. The resultant was subjected to reaction at 80° C. for 24 hours for solubilization, the resultant was cooled, and it was then washed with 500 ml of RO water. The washed resin was subjected to extraction 3 times with 100 ml of a 5% triethylamine/10% acetonitrile solution. After the obtained extracts had been mixed with each other, the mixture was solidified to dryness with the use of a rotary evaporator. The dried extract was dissolved in RO water and then lyophilized. Samples containing the resulting dry products at 3.00, 1.50, 0.75, 0.375, and 0.188 mg/ml were prepared and used to prepare the standard calibration curve for collagen peptide quantification.

(3-2) Measurement of Peptide Amount

The amount of the collagen peptide obtained in (2) was measured using the BCA protein assay kit (manufactured by PIERCE). The BCA protein assay reagent A was mixed with the BCA protein assay reagent B at a ratio of 50:1, and the resultant was designated as the BCA reagent. The sample (100 μl) was mixed with 2 ml of the BCA reagent, the mixture was incubated at 37° for 15 minutes, and the absorbance was measured at 562 nm. The absorbance was measured using a digital colorimeter (mini photo 10, Sanshin Kogyo). The amount of the peptide was determined on the basis of the collagen peptide standard calibration curved prepared in (3-1).

Table 1 and Table 2 show the results of measurements after the reaction had been conducted for 24 hours. In the recovered supernatant, the amount of the collagen peptide (the non-adsorbed peptide) was 3.65 g and the yield was 73%. In the recovered eluate, the amount of the collagen peptide (the adsorbed peptide) was 0.86 g and the yield was 17%.

TABLE 1

Yield of non-adsorbed peptide (reaction time: 24 hours)

|  | 1st | 2nd | 3rd | 4th | 5th | 6th |
|---|---|---|---|---|---|---|
| Liquid (g) | 82.27 | 74.25 | 76.85 | 61.26 | 60.43 | 62.59 |
| Protein (g) | 0.091 | 0.283 | 0.333 | 0.378 | 0.513 | 0.769 |
| Protein (accumulated) (g) | 0.091 | 0.374 | 0.707 | 1.084 | 1.598 | 2.367 |

|  | 7th | 8th | 9th | 10th | 11th | 12th/washing |
|---|---|---|---|---|---|---|
| Liquid (g) | 66.08 | 62.60 | 62.847 | 69.53 | 72.40 | 110.24 |
| Protein (g) | 0.483 | 0.209 | 0.128 | 0.195 | 0.152 | 0.116 |
| Protein (accumulated) (g) | 2.850 | 3.059 | 3.187 | 3.382 | 3.534 | 3.650 |
| Yield (accumulated) (%) |  |  |  |  |  | 73 |

TABLE 2

Yield of adsorbed peptide (reaction time: 24 hours)

|  | Extract |
|---|---|
| Liquid (g) | 119.29 |
| Protein (g) | 0.858 |
| Yield (accumulated) (%) | 17 |

Table 3 and Table 4 show the results of measurements after the reaction had been conducted for 48 hours. In the recovered supernatant, the amount of the collagen peptide (the non-adsorbed peptide) was 3.58 g and the yield was 72%. In the recovered eluate, the amount of the collagen peptide (the adsorbed peptide) was 0.77 g and the yield was 15%.

TABLE 3

Yield of non-adsorbed peptide (reaction time: 48 hours)

|  | 1st | 2nd | 3rd | 4th | 5th |
|---|---|---|---|---|---|
| Liquid (g) | 84.87 | 75.61 | 69.83 | 74.31 | 70.76 |
| Protein (g) | 0.147 | 0.389 | 0.568 | 0.788 | 0.798 |
| Protein (accumulated) (g) | 0.147 | 0.536 | 1.103 | 1.891 | 2.689 |

|  | 6th | 7th | 8th | Wash solution |
|---|---|---|---|---|
| Liquid (g) | 73.04 | 70.70 | 69.87 | 78.36 |
| Protein (g) | 0.431 | 0.246 | 0.165 | 0.053 |
| Protein (accumulated) (g) | 3.120 | 3.366 | 3.531 | 3.584 |
| Yield (accumulated) (%) |  |  |  | 72 |

TABLE 4

| Yield of adsorbed peptide (reaction time: 48 hours) | |
| --- | --- |
| | Extract |
| Liquid (g) | 143.6 |
| Protein (g) | 0.773 |
| Yield (accumulated) (%) | 15 |

As described above, there are no significant differences in terms of yield between the reaction time of 24 hours and that of 48 hours. When the reaction time is 48 hours, the frequency of recovery procedures can be lower. Thus, it is more efficient if the reaction is conducted for 48 hours.

(4) Analysis of Molecular Weight Distribution of Peptide Mixture

The molecular weight distribution of the collagen peptide obtained in (2) was measured via gel filtration chromatography. The measurement conditions are described below.

a) HPLC apparatus: pump (GL-7410, GL Sciences), autosampler (GL-7420, GL Sciences), column oven (CO631C, GL Sciences), UV detectors (SPD-10AV, Shimadzu Corporation; L-4200, Hitachi Co, Ltd.), RI detector (GL-7454, GL Sciences), and vacuum degasser (AG-14, Gastorr).

b) Column: TSKgel G3000SWXL (7.8×300 mm, 5 μm), Tosoh Corporation c) Mobile phase: 50 mM of sodium phosphate buffer/50 mM sodium chloride (pH 7.0)

d) Flow rate: 0.5 ml/min e) Temperature: 20° C.

f) Measurement wavelength: 215 nm, 280 nm g) Standard sample for molecular weight measurement: A standard solution for molecular weight measurement was prepared to comprise Shodex STANDARD P-82 (Showa Denko K.K.) at 0.1%.

Figure 4:
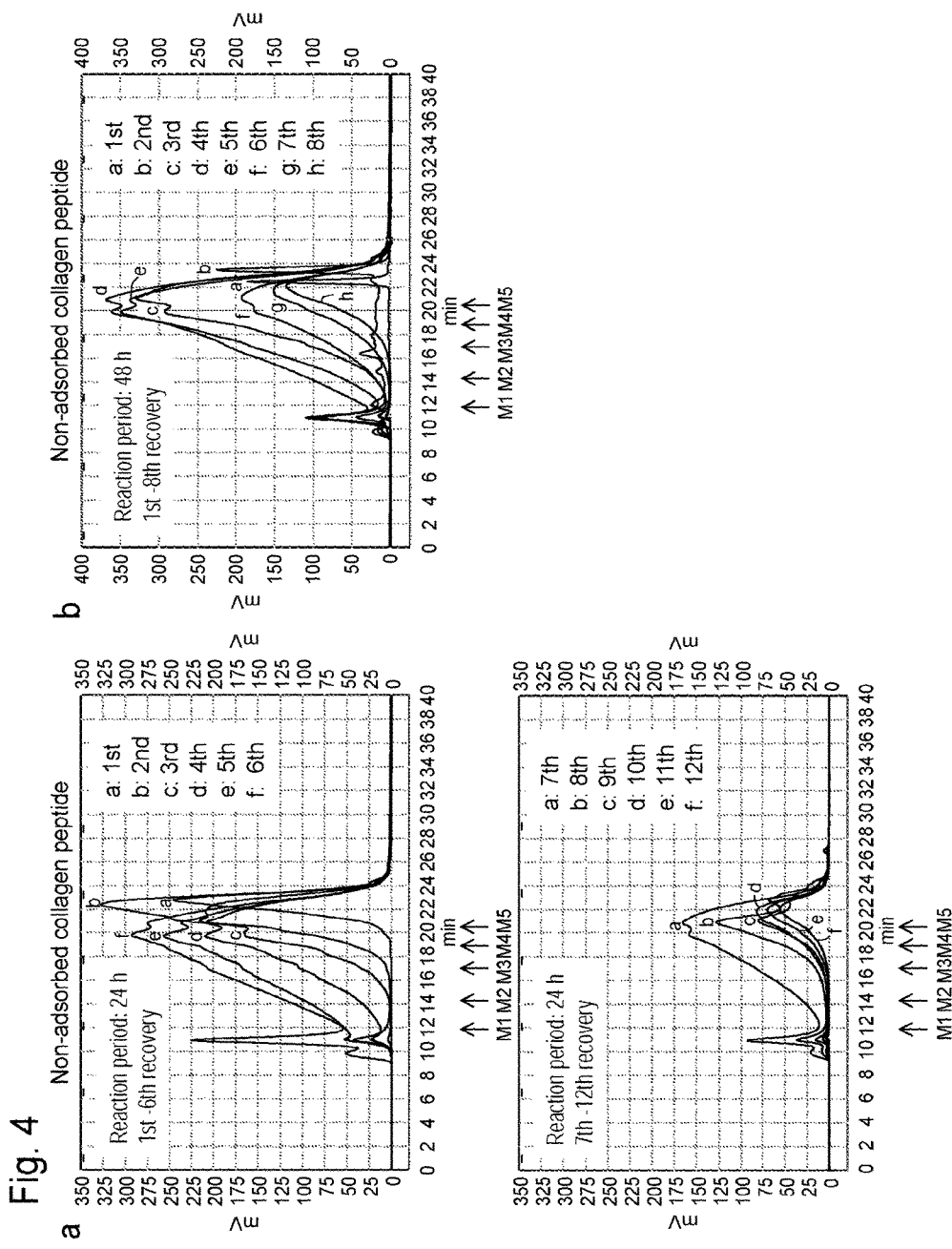
FIG. 4*a* shows the molecular weight distribution of a degradation product of a water-insoluble polymeric compound in a fraction that has not adsorbed to a solid acid catalyst (i.e., a collagen peptide obtained from the *Rhopilema esculenta* umbrella) (reaction time: 24 hours; upper diagram: the first to the sixth recovered liquids; lower diagram: the seventh to the twelfth recovered liquids; the molecular weights of pullulan standards: M1: 112 kDa; M2: 47.3 kDa; M3: 22.8 kDa; M4: 11.8 kDa; M5: 5.9 kDa).
FIG. 4*b* shows molecular weight distribution of a degradation product of a water-insoluble polymeric compound in a fraction that has not adsorbed to a solid acid catalyst (i.e., a collagen peptide obtained from the *Rhopilema esculenta* umbrella) (reaction time: 48 hours; the molecular weights of pullulan standards: M1: 112 kDa; M2: 47.3 kDa; M3: 22.8 kDa; M4: 11.8 kDa; M5: 5.9 kDa).

FIG. 4 shows molecular weight distribution of a collagen peptide (a non-adsorbed peptide) in a supernatant (the molecular weights of pullulan standards: M1: 112 kDa; M2: 47.3 kDa; M3: 22.8 kDa; M4: 11.8 kDa; M5: 5.9 kDa). After the reaction had been conducted for 24 hours, a sharp peak was detected at 5.9 kDa or less in terms of pullulan molecular weight standards in the first and the second recovery procedures, and, thereafter, a broad peak that had shifted toward the high-molecular-weight side was detected (FIG. 4a). After the reaction had been conducted for 48 hours, a slight peak shift from the high-molecular-weight side toward the low-molecular-weight side was observed (FIG. 4b).

FIG. 5 shows molecular weight distribution of a collagen peptide (an adsorbed peptide) in an eluate (the molecular weights of pullulan standards: M1: 112 kDa; M2: 47.3 kDa; M3: 22.8 kDa; M4: 11.8 kDa; M5: 5.9 kDa). The molecular weight of the adsorbed peptide was less than that of the non-adsorbed peptide, and the maximal peak was 5.9 kDa or less. Regardless of the reaction time, substantially the same molecular weight distribution was observed in the case of the reaction conducted for 24 hours as that observed in the case of the reaction conducted for 48 hours.

Example 2

Solubilization and Molecular Weight Reduction of Sericin (1) Solubilization and Molecular Weight Reduction of Sericin Using Solid Acid Catalyst Sericin powder (1 g, Kogensha Co. Ltd.) was wetted with 90 ml of RO water overnight, it was then mixed with 10 ml of cation exchange resin (TOYOPEARL SP-550C), and the mixture was thoroughly agitated. The resultant was subjected to reaction at 80° C. for 24 hours for solubilization, the resultant was cooled, and the supernatant containing the sericin peptide was then recovered. Subsequently, sericin powder was wetted overnight in the same manner as described above, the wet powder was added to the above cation exchange resin after the supernatant was recovered, the amount of the solution was adjusted to 100 ml with the addition of RO water, and the solution was thoroughly agitated. The resultant was subjected to reaction at 80° C. for 24 hours, and the supernatant was recovered again. This procedure was repeated 3 more times (and the first to the fifth recovery procedures were completed). Sericin powder was subjected to each procedure in an equivalent amount (5 g in total). RO water was added to the remaining cation exchange resin, so as to adjust the amount of the solution to 100 ml, and the resultant was thoroughly agitated. After the reaction had been conducted at 80° C. for 24 hours, the supernatant was recovered. This procedure was repeated 6 more times (and the sixth to the eleventh recovery procedures were completed). The remaining cation exchange resin was washed with 60 ml of RO water. The recovered supernatant was mixed with the wash solution, and a solution of the sericin peptide with a molecular weight (Mp) of 5.9 kDa or less, which had not adsorbed to the cation exchange resin, was obtained.

Figure 6:
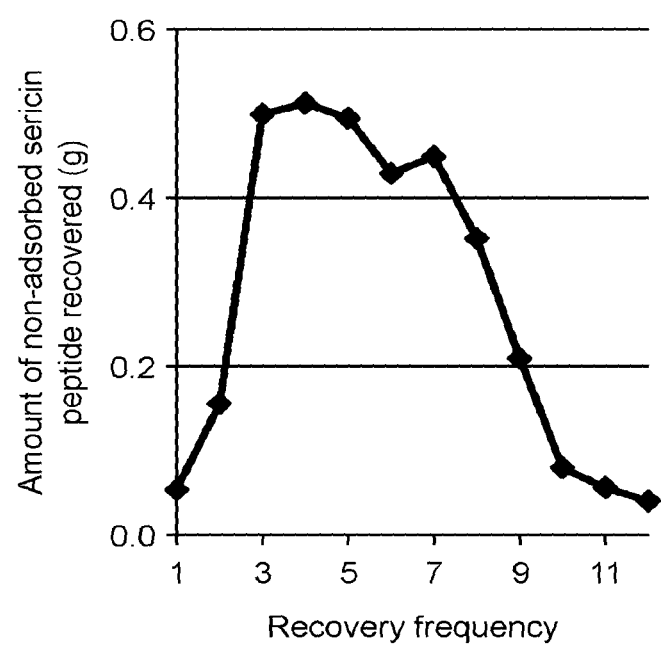
FIG. 6 shows a transition in the amount of a degradation product of a water-insoluble polymeric compound (a sericin peptide) recovered from a fraction that has not adsorbed to a solid acid catalyst.

FIG. 6 shows the transition of the amount of the sericin peptide (i.e., the non-adsorbed peptide) in the recovered supernatant.

Subsequently, 60 ml of 0.5 M NaCl was added to the washed cation exchange resin, and a degradation product containing the sericin peptide was eluted from the resin. This procedure was repeated 3 more times, and all the eluates were mixed with each other. Thus, a solution of the sericin peptide with a molecular weight (Mp) of 5.9 kDa or less, which had adsorbed to the cation exchange resin, was obtained.

(2) Quantification of Peptide Mixture (2-1) Preparation of Standard Sericin Peptide Sample The solution of the sericin peptide, which had not adsorbed to the cation exchange resin obtained in (1), was lyophilized. Samples containing the resulting dry products at 0.75, 0.375, 0.188, and 0.094 mg/ml were prepared and used to prepare the standard calibration curve for sericin peptide quantification.

(2-2) Measurement of Sericin Peptide Amount

The amount of the sericin peptide obtained in (1) was measured in the same manner as in Example 1 (3-2), except for the use of the standard calibration curve for sericin peptide quantification.

Table 5 and Table 6 show the results of measurements. In the recovered supernatant, the amount of the sericin peptide (the non-adsorbed peptide) was 3.36 g and the yield was 67%. In the recovered eluate, the amount of the sericin peptide (the adsorbed peptide) was 0.21 g and the yield was 4%.

TABLE 5

| Yield of non-adsorbed peptide | | | | | | |
|---|---|---|---|---|---|---|
| | 1st | 2nd | 3rd | 4th | 5th | 6th |
| Liquid (g) | 76.47 | 68.16 | 64.38 | 56.03 | 52.38 | 47.79 |
| Protein (g) | 0.054 | 0.156 | 0.499 | 0.512 | 0.494 | 0.429 |
| Protein (accumulated) (g) | 0.054 | 0.209 | 0.708 | 1.220 | 1.714 | 2.143 |
| | 7th | 8th | 9th | 10th | 11th | 12th/washing |
| Liquid (g) | 50.75 | 52.51 | 48.21 | 52.55 | 56.53 | 128.44 |
| Protein (g) | 0.449 | 0.351 | 0.209 | 0.080 | 0.056 | 0.068 |
| Protein (accumulated) (g) | 2.592 | 2.943 | 3.153 | 3.233 | 3.289 | 3.357 |
| Yield (accumulated) (%) | | | | | | 67 |

TABLE 6

| Yield of adsorbed peptide | |
|---|---|
| | Extract |
| Liquid (g) | 169.64 |
| Protein (g) | 0.21 |
| Yield (accumulated) (%) | 4 |

(3) Analysis of Molecular Weight Distribution of Peptide Mixture

The molecular weight distribution of the sericin peptide obtained in (1) was measured via gel filtration chromatography in accordance with the same measurement conditions employed in Example 1.

FIG. 7 shows molecular weight distribution of a sericin peptide (a non-adsorbed peptide) in a supernatant (the molecular weights of pullulan standards: M1: 112 kDa; M2: 47.3 kDa; M3: 22.8 kDa; M4: 11.8 kDa; M5: 5.9 kDa). While a sharp peak was detected at 5.9 kDa or less in terms of pullulan molecular weight standards in the first and the second recovery procedures, a broad peak shifted toward the high-molecular-weight side was detected thereafter.

Figure 8:
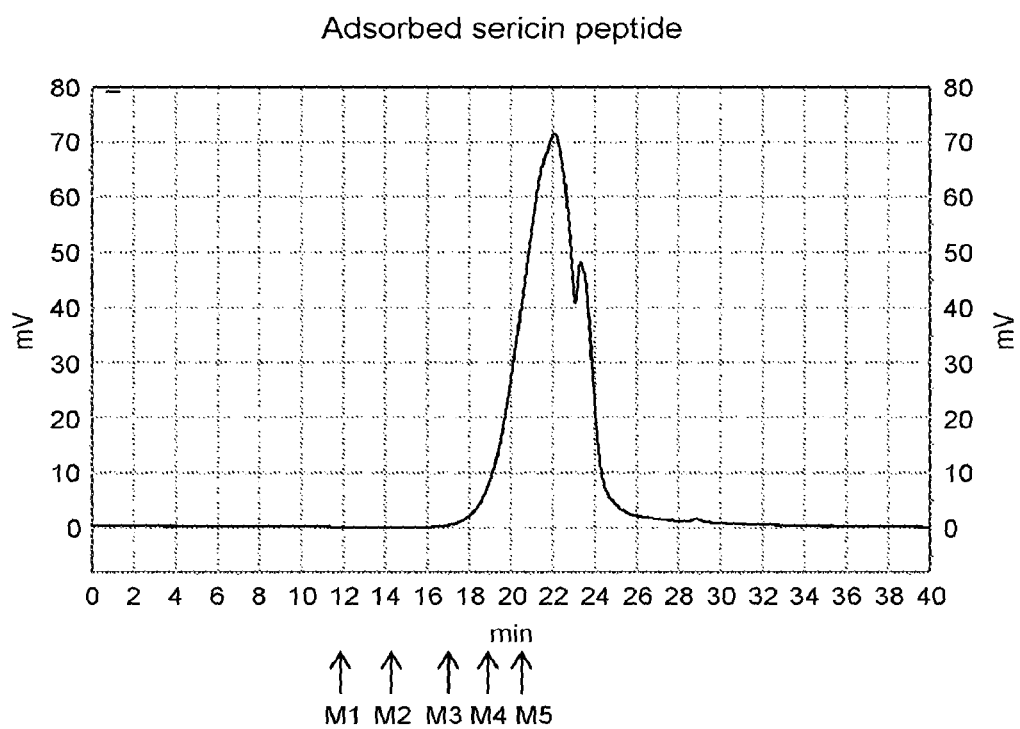
FIG. 8 shows molecular weight distribution of a degradation product of a water-insoluble polymeric compound (a sericin peptide) in a fraction that has adsorbed to a solid acid catalyst (the molecular weights of pullulan standards: M1: 112 kDa; M2: 47.3 kDa; M3: 22.8 kDa; M4: 11.8 kDa; M5: 5.9 kDa).

FIG. 8 shows molecular weight distribution of a sericin peptide (an adsorbed peptide) in an eluate (the molecular weights of pullulan standards: M1: 112 kDa; M2: 47.3 kDa; M3: 22.8 kDa; M4: 11.8 kDa; M5: 5.9 kDa). The maximal peak of the adsorbed peptide did not significantly differ from the peak of the non-adsorbed peptide observed at the first, second, and seventh to twelfth recovery procedures.

Example 3

Solubilization and Molecular Weight Reduction of Keratin (1) Solubilization and Molecular Weight Reduction of Keratin Using Solid Acid Catalyst Keratin powder (1 g, Nacalai Tesque, Inc.) was wetted with 90 ml of RO water overnight, it was then mixed with 10 ml of cation exchange resin (TOYOPEARL SP-550C), and the mixture was thoroughly agitated. The resultant was subjected to reaction at 100° C. for 48 hours for solubilization, the resultant was cooled, and the supernatant containing the keratin peptide was then recovered. Subsequently, keratin powder was wetted overnight in the same manner as described above, the wet powder was added to the above cation exchange resin after the supernatant was recovered, the amount of the solution was adjusted to 100 ml with the addition of RO water, and the solution was thoroughly agitated. The resultant was subjected to reaction at 100° C. for 48 hours, and the supernatant was recovered again. This procedure was repeated 3 more times (and the first to the fifth recovery procedures were completed). Keratin powder was subjected to each procedure in an equivalent amount (5 g in total). RO water was added to the remaining cation exchange resin, so as to adjust the amount of the solution to 100 ml, and the resultant was thoroughly agitated. After the reaction had been conducted at 100° C. for 48 hours, the supernatant was recovered. This procedure was repeated 2 more times (and the sixth to the eighth recovery procedures were completed). The remaining cation exchange resin was washed with 80 ml of RO water. The recovered supernatant was mixed with the wash solution, and a solution of the keratin peptide with a molecular weight (Mp) of 5.9 kDa or less, which had not adsorbed to the cation exchange resin, was obtained.

Subsequently, 50 ml of 0.5 M NaCl was added to the washed cation exchange resin, and a degradation product containing the keratin peptide was eluted from the resin. This procedure was repeated 2 more times, and all the eluates were mixed with each other. Thus, a solution of the keratin peptide with a molecular weight (Mp) of 5.9 kDa or less, which had adsorbed to the cation exchange resin, was obtained.

(2) Quantification of Peptide Mixture (2-1) Preparation of Standard Keratin Peptide Sample The solution of the keratin peptide adsorbed to the ion exchange resin obtained in (1) (the eluate) was lyophilized. Samples containing the resulting dry products at 0.75, 0.375, 0.188, and 0.094 mg/ml were prepared and used to prepare the standard calibration curve for keratin peptide quantification.

(2-2) Measurement of Keratin Peptide Amount

The amount of the keratin peptide in the eluate among the keratin peptide obtained in (1) was measured in the same manner as in Example 1 (3-2), except for the use of the standard calibration curve for keratin peptide quantification. Regarding the amount of the keratin peptide in the supernatant (including the wash solution), the supernatant was lyophilized, and dry weight of the keratin peptide was determined.

In the recovered supernatant, the amount of the keratin peptide (the non-adsorbed peptide) was 2.65 g and the yield was 53%. In the recovered eluate, the amount of the keratin peptide (the adsorbed peptide) was 0.20 g and the yield was 4%.

(3) Analysis of Molecular Weight Distribution of Peptide Mixture

The molecular weight distribution of the keratin peptide obtained in (1) was measured via gel filtration chromatography in accordance with the same measurement conditions employed in Example 1.

FIG. 9 shows molecular weight distribution of a keratin peptide (a non-adsorbed peptide) in a supernatant (the molecular weights of pullulan standards: M1: 112 kDa; M2: 47.3 kDa; M3: 22.8 kDa; M4: 11.8 kDa; M5: 5.9 kDa). A sharp peak was detected at 5.9 kDa or less in terms of pullulan molecular weight standards in the first to the fifth and the sixth to eighth recovery procedures.

Figure 10:
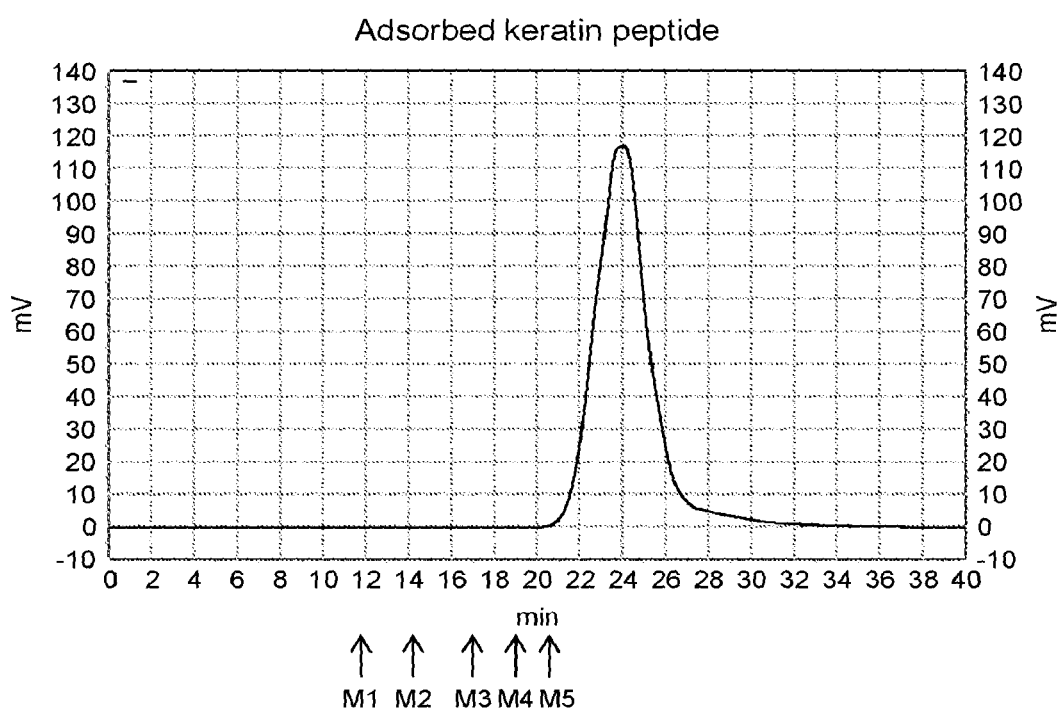
FIG. 10 shows molecular weight distribution of a degradation product of a water-insoluble polymeric compound (a keratin peptide) in a fraction that has adsorbed to a solid acid catalyst (the molecular weights of pullulan standards: M1: 112 kDa; M2: 47.3 kDa; M3: 22.8 kDa; M4: 11.8 kDa; M5: 5.9 kDa).

FIG. 10 shows molecular weight distribution of a keratin peptide (an adsorbed peptide) in an eluate. The maximal peak of the adsorbed peptide did not significantly differ from that of the non-adsorbed peptide.

Example 4

Solubilization and Molecular Weight Reduction of Agar (1) Solubilization and Molecular Weight Reduction of Agar Using Solid Acid Catalyst Agar powder (1 g, Kanto Chemical Co., Inc.) was suspended in 90 ml of RO water, it was mixed with 10 ml of cation exchange resin (TOYOPEARL SP-550C), and the mixture was thoroughly agitated. The resultant was subjected to reaction at 100° C. for 24 hours for solubilization, the resultant was cooled, and the supernatant containing the agar oligosaccharide was then recovered. Subsequently, agar powder was wetted overnight in the same manner as described above, the wet powder was added to the above cation exchange resin after the supernatant was recovered, the amount of the solution was adjusted to 100 ml with the addition of RO water, and the solution was thoroughly agitated. The resultant was subjected to reaction at 100° C. for 24 hours, and the supernatant was recovered again. This procedure was repeated 3 more times (and the first to the fifth recovery procedures were completed). The agar powder was subjected to each procedure in an equivalent amount (5 g in total).

RO water was added to the remaining cation exchange resin, so as to adjust the amount of the solution to 100 ml, and the resultant was thoroughly agitated. After the reaction had been conducted at 100° C. for 24 hours, the supernatant was recovered. This procedure was repeated 2 more times (and the sixth to the eighth recovery procedures were completed). The remaining cation exchange resin was washed with 80 ml of RO water. The recovered supernatant was mixed with the wash solution, and a solution of the agar oligosaccharide, which had not adsorbed to the cation exchange resin, was obtained.

Figure 11:
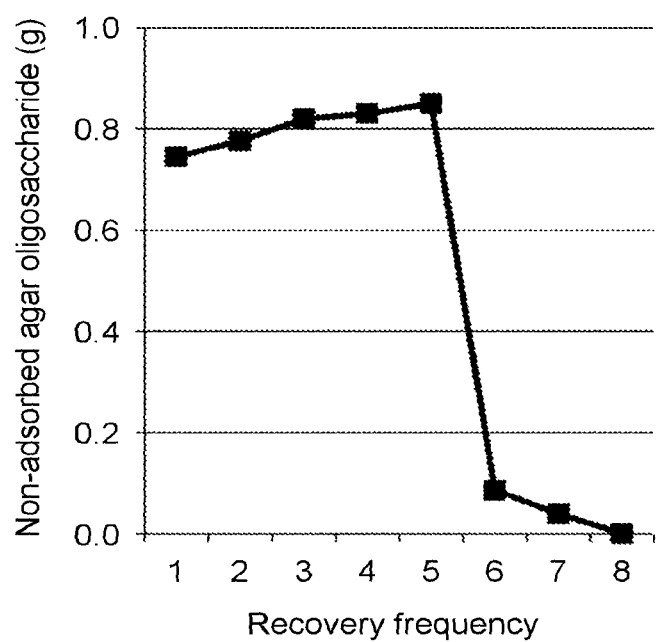
FIG. 11 shows a transition in the amount of a degradation product of a water-insoluble polysaccharide (an agar oligosaccharide) recovered from a fraction that has not adsorbed to a solid acid catalyst.

FIG. 11 shows the transition of the amount of the agar oligosaccharide (i.e., the non-adsorbed oligosaccharide) in the recovered supernatant.

Subsequently, 50 ml of 0.5 M NaCl was added to the washed cation exchange resin, and a degradation product containing the agar oligosaccharide was eluted from the resin. This procedure was repeated 2 more times, and all the eluates were mixed with each other. Thus, a solution of the agar oligosaccharide, which had adsorbed to the cation exchange resin, was obtained.

(2) Quantification of Oligosaccharide Mixture

Regarding the amount of the agar oligosaccharide in the supernatant (including the wash solution) among the agar oligosaccharides obtained in (1), the supernatant was lyophilized, and dry weight of the agar oligosaccharide was determined. The amount of the agar oligosaccharide in the eluate was determined by the phenol-sulfuric acid method described below. At the outset, 1.0 ml of a 5% phenol solution was added to and mixed with 1.0 ml of the sample. Subsequently, 5.0 ml of concentrated sulfuric acid was directly added dropwise thereto rapidly. The resulting mixture was allowed to stand at room temperature for 10 minutes and then cooled in a water bath for 10 minutes. The absorbance was measured at 470 nm. The absorbance was measured using a digital colorimeter (mini photo 10, San-shin Kogyo). Samples containing the glucose at 50, 100, and 150 mg/ml were prepared and used to prepare the standard calibration curve.

Table 7 shows the results of measurements. In the recovered supernatant, the amount of the agar oligosaccharide (the non-adsorbed oligosaccharide) was 4.15 g and the yield was 83%.

TABLE 7

|  | 1st | 2nd | 3rd | 4th | 5th | 6th |
| --- | --- | --- | --- | --- | --- | --- |
| Oligosaccharide (g) | 0.745 | 0.776 | 0.820 | 0.831 | 0.851 | 0.087 |
| Oligosaccharide (accumulated) (g) | 0.745 | 1.521 | 2.341 | 3.171 | 4.021 | 4.108 |
| Yield (accumulated) (g) |  |  |  |  |  |  |

|  | 7th | 8th | Wash solution |
| --- | --- | --- | --- |
| Oligosaccharide (g) | 0.004 | 0.002 | 0.000 |
| Oligosaccharide (accumulated) (g) | 4.148 | 4.149 | 4.149 |
| Yield (accumulated) (%) |  |  | 83 |

No agar oligosaccharide was detected in the recovered eluate and the yield was 0%.

(3) Analysis of Molecular Weight Distribution of Oligosaccharide Mixture

The molecular weight distribution of the agar oligosaccharide obtained in (1) was measured via gel filtration chromatography. Measurement was carried out under the same conditions as employed in Example 1, except for the use of the TSKgel G-OLIGO-PW column (7.8×300 mm, Tosoh Corporation). As control samples, the standard sample for molecular weight measurement (Shodex STANDARD P-82, Showa Denko K.K., molecular weight: 5.9 kDa), a monosaccharide (glucose), a disaccharide (sucrose), and a trisaccharide (raffinose) were used.

Figure 12:
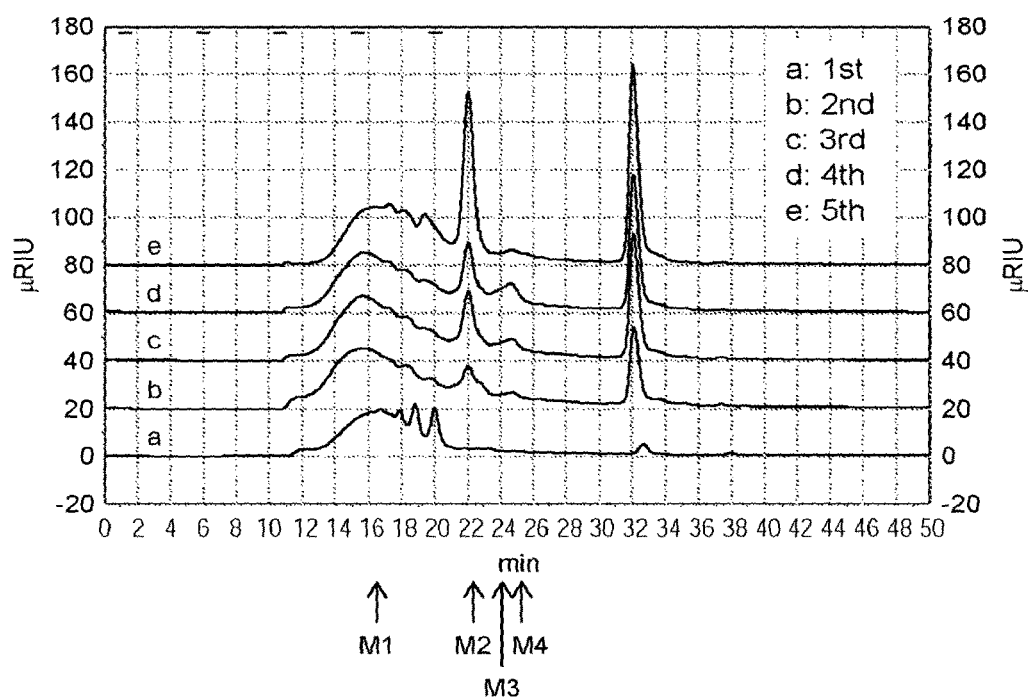
FIG. 12 shows molecular weight distribution of a degradation product of a water-insoluble polysaccharide (an agar oligosaccharide) in a fraction that has not adsorbed to a solid acid catalyst (control substance M1: 5.9 kDa (Shodex STANDARD P-82, Showa Denko K.K.); M2: trisaccharide (raffinose); M3: disaccharide (sucrose); M4: monosaccharide (glucose)).

FIG. 12 shows molecular weight distribution of the agar oligosaccharide (the non-adsorbed oligosaccharide) in the supernatant (control substance M1: 5.9 kDa (M1: Shodex STANDARD P-82, Showa Denko K.K.); M2: trisaccharide (raffinose); M3: disaccharide (sucrose); M4: monosaccharide (glucose)). A broad peak corresponding to the trisaccharide (raffinose) or larger oligosaccharides was observed in each of the first to the fifth recovery. procedures.

INDUSTRIAL APPLICABILITY

The present invention is applicable in the fields for the production of functional peptides or functional oligosaccharides that are starting materials of pharmaceutical products, food and beverage products, and cosmetic products.

All publications, patents, and patent applications cited herein are incorporated herein by reference in their entirety.

The invention claimed is:
1. A method for producing a degradation product of a water-insoluble polymeric compound, the method comprising, in the following order:
(A) bringing a water-insoluble polymeric compound in a first aqueous medium into contact with a cation exchange resin to form a first mixture, heating the first mixture, and recovering a first supernatant comprising the degradation product;

(B) adding a second aqueous medium to the cation exchange resin to form a second mixture, agitating and heating the second mixture, and recovering a second supernatant comprising the degradation product;

(C) washing the cation exchange resin of (B) with a third aqueous medium and recovering a wash solution comprising the degradation product;

(D) mixing the supernatant recovered in (A), the supernatant recovered in (B), and the wash solution recovered in (C) to obtain a fraction that has not adsorbed to the cation exchange resin and that comprises the degradation product; and (E) eluting the adsorbed fraction from the cation exchange resin and recovering an eluate, so as to obtain a fraction that has adsorbed to the cation exchange resin comprising residual degradation product, wherein the water-insoluble polymeric compound is a protein, a peptide or a saccharide, and wherein (A) and (B) are repeated 2 to 8 times when the water-insoluble polymeric compound is a protein or peptide or wherein (A) and (B) are repeated 2 to 5 times when the water-insoluble compound is a saccharide.

2. The method according to claim 1, wherein the water-insoluble polymeric compound is a water-insoluble protein or a water-insoluble polysaccharide.

3. The method according to claim 1, further comprising soaking the water-insoluble polymeric compound in the first aqueous medium before the bringing of the water-insoluble polymeric compound into contact with the cation exchange resin.

4. The method according to claim 1, wherein an amount of the water-insoluble polymeric compound is 0.01- to 0.5-fold relative to an amount of the cation exchange resin by mass.

5. The method according to claim 1, wherein, in (A), an amount of the first aqueous medium used when bringing the water-insoluble polymeric compound into contact with the cation exchange resin is adjusted to 1- to 50-fold relative to an amount of the cation exchange resin by mass.

6. The method according to claim 1, wherein the heating treatment in (A) and (B) is carried out at 40° C. to 160° C. for 0.1 to 168 hours.

7. The method according to claim 1, wherein (A) and (B) are each repeated a plurality of times until the yield of the degradation product of the water-insoluble polymeric compound in the non-adsorbed fraction reaches 50% or higher by mass.

8. The method according to claim 1, wherein the supernatant in (A) comprises at least 65% by mass of the produced degradation product.

9. The method according to claim 1, wherein the supernatant in (A) comprises at least 80% by mass of the produced degradation product.

10. The method according to claim 1, wherein the degradation product is recovered in a non-adsorbed fraction.

11. The method according to claim 1, wherein the fraction that has not adsorbed to the cation exchange resin in (D) comprises at least 65% by mass of the produced degradation product.

12. The method according to claim 1, wherein the fraction that has not adsorbed to the cation exchange resin in (D) comprises at least 80% by mass of the produced degradation product.

13. The method according to claim 1, wherein the water-insoluble polymeric compound is a water-insoluble polysaccharide.

* * * * *